(12) United States Patent
Liang

(10) Patent No.: US 7,345,188 B2
(45) Date of Patent: Mar. 18, 2008

(54) PROCESS FOR PREPARING BENZHYDRYLTHIOACETAMIDE

(75) Inventor: Sidney Liang, Olivette, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 249 days.

(21) Appl. No.: 10/570,243

(22) PCT Filed: Oct. 22, 2004

(86) PCT No.: PCT/US2004/034975

§ 371 (c)(1),
(2), (4) Date: Mar. 3, 2006

(87) PCT Pub. No.: WO2005/042479

PCT Pub. Date: May 12, 2005

(65) Prior Publication Data

US 2008/0027240 A1    Jan. 31, 2008

(51) Int. Cl.
*C07C 323/00*  (2006.01)
*C07C 315/00*  (2006.01)
*C07C 317/00*  (2006.01)

(52) U.S. Cl. .......................................... 560/15; 568/36
(58) Field of Classification Search ..................... None
See application file for complete search history.

(56) References Cited

U.S. PATENT DOCUMENTS 4,177,290 A * 12/1979 Lafon .......................... 514/618

* cited by examiner

*Primary Examiner*—Paul A. Zucker

(57) ABSTRACT

The present invention is directed to an improved process for preparing modafinil wherein benzhydrylthioacetate is prepared in high yield and purity by the reaction of a haloacetate with the reaction product of thiourea and benzhydrol. The reaction employing the haloacetate is conducted in a solvent comprising an organic solvent such as methanol having dissolved therein an organic base or an inorganic basic salt such as sodium bicarbonate. The resulting benzhydrylthioacetate can be amidated and then oxidized to provide the pharmaceutical grade modafinil in high yield and purity.

33 Claims, No Drawings

PROCESS FOR PREPARING BENZHYDRYLTHIOACETAMIDE

FIELD OF THE INVENTION

This invention relates to an improved process for preparing modafinil wherein the intermediate, benzhydrylthioacetate is prepared in a reaction medium comprising an organic solvent having dissolved therein an organic base or an inorganic basic salt. The acetate thus produced is amidated and then oxidized to provide benzhydrylsulphinylacetamide, commonly known as modafinil.

BACKGROUND OF THE INVENTION

Lafon disclosed modafinil and other similar compounds in U.S. Pat. No. 4,177,290 as having pharmaceutical activity on the central nervous system. In a typical prior art process, benhydrylthioacetic acid is halogenated with thionyl chloride. The chloride is then converted to the amide in methylene chloride with ammonia. The amide is then oxidized with hydrogen peroxide to provide benzhydrylsulphinylacetamide. Other derivatives of modafinil as well as methods of preparation and purification are disclosed in U.S. Pat. No. 4,127,722. However, the amide appears to be the compound of choice among the many derivatives now known.

Interest in the Lafon compounds has increased in recent years because these compounds have been discovered to have beneficial effects in the treatment of a wide variety of diseases in mammals including humans. Although first noted as a treatment for narcolepsy, more recent patents and technical publications have listed such compounds as beneficial in the treatment of Parkinson's disease, urinary incontinence, Alzheimer's disorder, ischemia and stroke. As the use of these compounds increased so has the demand for greater volumes while maintaining the highest state of purity and also avoiding process chemicals of high environmental risk.

Lafon also disclosed the use of an intermediate, a racemic mixture of benzhydrylsulphinylacetic acid to prepare an isomer of modafinil in U.S. Pat. No. 4,927,855, referring to French patent 2,326,181B. The racemic mixture of the acid was reacted with the (−)-α-methylbenzylamine to provide the (−)-benzhydrylsulphinylacetate of (−)-methylbenzylamine which is acidified with concentrated hydrochloric acid to provide (−)benzyhydrylsulphinylacetic acid. The levo-acid thus produced was then reacted with methylsulfate in water and sodium bicarbonate to provide methyl(−)benzhydrylsulphinylacetate. The acetate was then amidated with ammonia gas to provide (−)benzhydrylsulphinylacetamide.

Numerous substituted thioacetamides are disclosed in U.S. Pat. No. 6,492,396 to Bacon et al. In one synthesis scheme benzhydrol is converted to a benzhydrylthiol by reaction with thiourea that is then converted by hydrolysis to a thiouronium moiety. Subsequently, the thiouronium is converted to an acid with chloroacetic acid. The benzhydrylthioacetic acid is treated in various ways depending upon the desired derivative. To prepare the amide the acid is reacted with ammonia or an appropriate amine in an organic solvent such as tetrahydrofuran or methylene chloride. Other thioacetamide derivatives are obtained by employing N-methylmorpholine and a thioacetic acid in dimethylformamide (DMF).

A procedure for the preparation of an acetamide intermediate for the production of modafinil is disclosed in published US application 2002/0183552. According to this application a three-step procedure for preparing modafinil is disclosed starting with benzhydrol (diphenylmethanol) that is employed to prepare the benzhydrylthiocarboxamidine salt by reaction with thiourea in hydrogen bromide. The bromide salt is then reacted with chloroacetamide in aqueous sodium hydroxide to produce diphenylmethylthioacetamide. The acetamide may then be oxidized by conventional means to produce modafinil. Typically, the oxidation is provided by a reaction with hydrogen peroxide in glacial acetic acid.

Because of the growing demand for large quantities of modafinil in a highly pure state there is needed a more efficient process for preparing the product. In particular, the production of highly pure acetamide intermediate is needed to improve overall process economics.

SUMMARY OF THE INVENTION

In accordance with this invention there is provided a novel process for the preparation of benzhydrylthioacetate by the reaction of a haloacetate with the reaction product of thiourea and benzhydrol. The improved process is conducted in a reaction medium comprising an organic solvent having dissolved therein an organic base or an inorganic basic salt. The resulting benzhydrylthioacetate is provided in high yield and purity and can be amidated and oxidized to provide the pharmaceutical modafinil.

The process of this invention provides improved yield and purity over known processes. The organic solvent provides the dual function of providing a solvent for the starting organic material while also providing a convenient reaction medium allowing relatively low temperature reactions to take place.

DETAILED DESCRIPTION OF THE INVENTION

The pharmaceutical modafinil is conveniently prepared in three steps including the novel step of this invention wherein 2-chloroacetate, an organic solvent and a basic salt is employed. First, benzhydrol 1 is reacted with thiourea 2 to provide a reaction product that is sometimes termed the benzhydrylthiocarboxamidine salt 3. This reaction is carried out in water in the presence of hydrogen halide, shown below as the bromide at a temperature of about 80° C. for a period of from about 1 to about 2 hours. However, it has been found that the chloride is preferred in this first step because there is produced less by product and higher efficiency. A solid benzhydrylthiocarboxamidine halide salt precipitates. The reaction may be described structurally as follows:

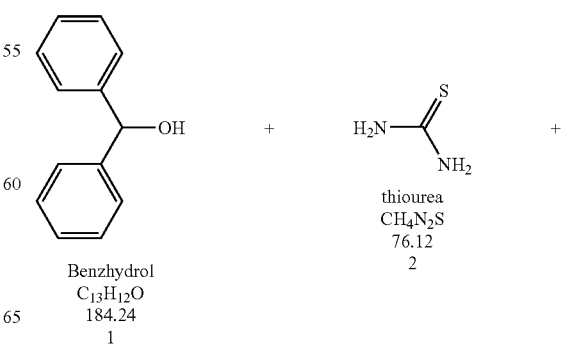

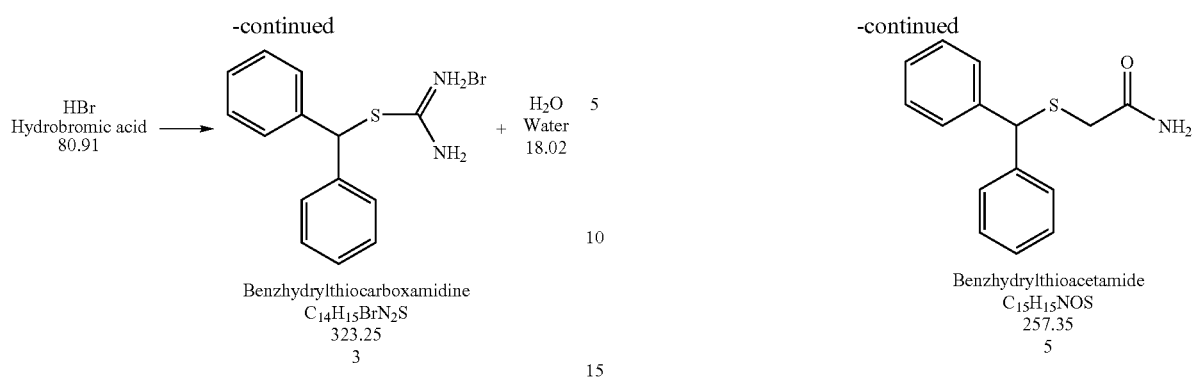

Benzhydrylthiocarboxamidine
C₁₄H₁₅BrN₂S
323.25
3

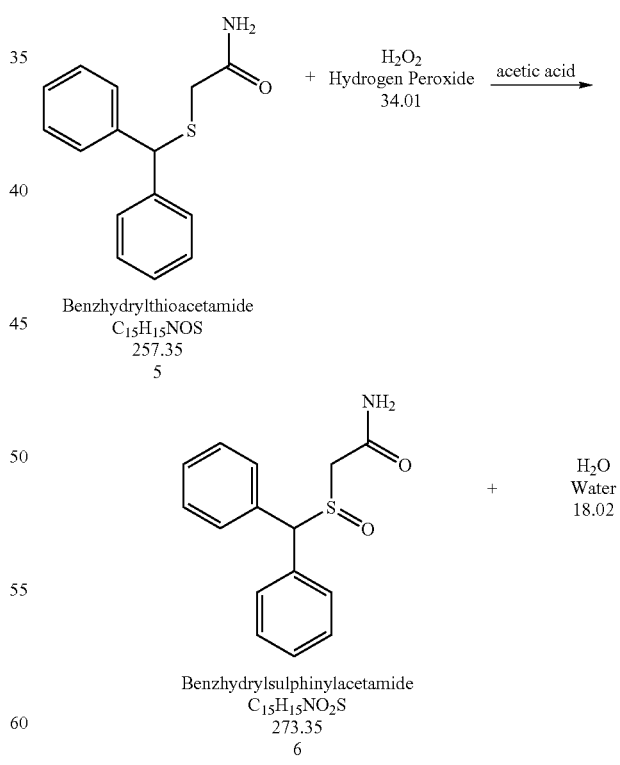

Benzhydrylthioacetamide
C₁₅H₁₅NOS
257.35
5

In the second step, the benzhydrylthiocarboxamidine bromide 3 salt solids are washed with water then placed in a reaction vessel together with methyl 2-chloroacetate 4, a basic salt and an organic solvent, such as methanol. This mixture is stirred to dissolve the bromide salt and to allow it to react to provide methyl benzhydrylthioacetate. Although the reaction is described with respect to the bromide salt, any other suitable salt may be employed. After formation of the acetate, it can be converted to the amide with ammonia without removal from the reaction vessel. This is conveniently accomplished by passing ammonia through the reaction mixture for about 1 hour followed by stirring for an additional 5 hours. When the reaction is completed the reaction mixture is diluted with water and a solid precipitate is separated. When washed with water, benzhydrylthioamide 5 is obtained in high yield and purity. The reaction may be described structurally as follows:

In the third step of the procedure to obtain modafinil in accordance with this invention, benzhydrylthioacetamide 5 is dissolved in acetic acid and then hydrogen peroxide is slowly charged to the solution while cooling to control the exothermic reaction. Typically the temperature is maintained below 22° C. to prevent undesired side reactions. After the reaction is completed, diluting the reaction mixture with water and separating the precipitate to obtain a crude racemic benzhydrylsulphinylacetamide 6 (modafinil) isolates the product. The crude product is typically refined by recrystallization in a solvent or a mixture of solvents including chloroform to obtain highly pure pharmaceutical grade modafinil in about 70% overall yield. The reaction may be described structurally as follows:

Step 2: Benzhydrylthioacetamide

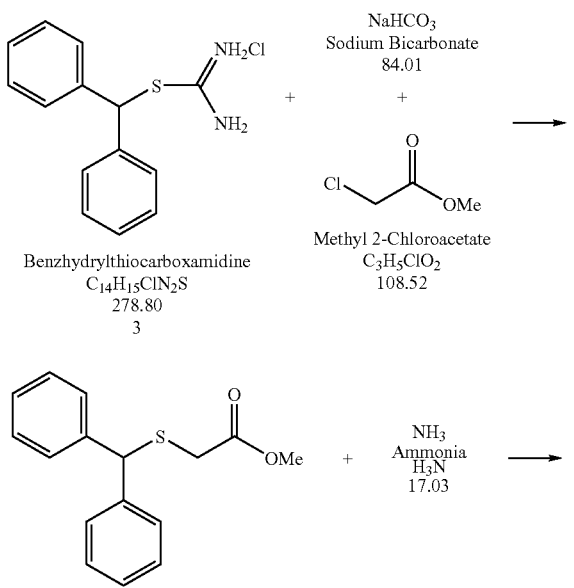

The term "alkali metal" encompasses lithium, sodium, potassium, cesium and rubidium; and the term "alkaline earth metal" includes beryllium, magnesium, calcium, strontium and barium. Typically, the preferred alkali metals are sodium and potassium while the preferred alkaline earth metal salts are calcium and magnesium.

Any suitable organic solvent can be employed in the process of this invention. The organic solvent must have some degree of solvating power with respect to the organic starting material benzhydrylthiocarboxamidine salt. Typically, such solvents include acetone and lower alkanols such as methanol, propanol, isopropanol, ethanol, butanol, sec-butyl alcohol and tert-butyl alcohol. However, it has been found that methanol is particularly useful.

The process of this invention, employing an organic solvent reaction medium containing a basic salt, produces isolated yields in the range of about 97% (based upon HPLC analysis) with the amount of each impurity at less than 3%. Such results represent significant yield improvements as well as a more efficient process compared to all other known methods. This process eliminates a process step and the use of thionyl chloride and benzene in comparison to the '290 patent. The process of this invention also eliminates the use of corrosive solutions, and byproducts, while still producing higher yields with very low impurities compared to the prior art processes such as those that employ sodium hydroxide with haloacetamide in the above described published application.

Any number of basic salts can be employed in the process of this invention. Salts may be employed that may only be slightly soluble in organic solvents. However, the presence of the salt in the reaction medium remains effective to promote the reaction in the particulate form. In particular, it is preferred to employ ammonium, alkali metal salts or alkaline earth metal salts. The sodium salt is preferred and the potassium salt is even more preferred. The anion of the salt is typically a sulfate, sulfide, phosphate, bicarbonate, nitrate, phosphonate, phosphinate and preferably a carbonate. Typical salts or basic organics included in the above description of salts are sodium sulfate, calcium sulfate, magnesium sulfate, sodium sulfide, magnesium sulfide, calcium sulfide, sodium phosphate, magnesium phosphate, calcium phosphate, potassium phosphate, sodium bicarbonate, calcium bicarbonate, magnesium bicarbonate, sodium nitrate, calcium nitrate, magnesium nitrate, sodium phosphonate, potassium phosphonate, magnesium phosphonate, calcium phosphonate, sodium phosphinate, potassium phosphinate, calcium phosphinate, magnesium phosphinate, potassium sulfate, potassium sulfide, potassium bicarbonate, potassium nitrate, potassium tripolyphosphate, sodium tripolyphosphate, sodium thiophosphate, potassium citrate, tetrapotassium pyrophosphate, ammonium phosphate, ammonium chloride, ammonium sulfate, ammonium bicarbonate, ammonium phosphinate, dimethylformamide, ammonium phosphonate, triethylamine, Hunig's base and the like. Potassium carbonate is preferred because it is readily soluble in water.

As used herein the term "halo-" refers to compounds containing a halogen selected from chlorine, fluorine, bromine and iodine.

Any number of acetates can be employed in the process of this invention. Typically the acetates are selected from lower alkyl straight or branched chain compounds containing from one to five carbon atoms. Most preferred are methyl, ethyl or propyl acetates.

The process of this invention has been found to be particularly advantageous over the prior art sodium hydroxide process wherein chloroacetamide employed. Said prior art process requires higher temperatures to help increase the yields since lower temperatures tend to produce significant amounts of impurities. A milder basic solution was thought to be sufficient enough to promote the reaction and at lower temperature conditions. Water and potassium carbonate were initially used, but byproducts were still produced. In a preferred embodiment, a mixture of methanol and potassium bicarbonate solution was employed to help dissolve the starting reagent and promote a more stable pH during the reaction. The amount of basic salt per equivalent of the total starting reagent benzhydrylthiocarboxamidine bromide salt employed in the process of this invention, is typically in the range of greater than about 0.1 molar equivalent.

In another aspect of this invention is the clean up of the final product, modafinil. It has been found that mixing it with chloroform best purified the final product. The preferred method is to then refluxing the mixture for a short period of time. The refluxed mixture is then cooled to a relatively low temperature, filtered and washed to provide a highly pure modafinil product. The use of methanol and/or methanol:/water solvent as disclosed in the original '290 patent to purify the modafinil was found to be inadequate or inefficient in obtaining pharmaceutically pure modafinil. Similar alcohol solvents such as ethanol and propanol also gave similar results wherein several impurities were significantly greater than 0.1%. Modafinil was only mildly soluble, at best, in alcoholic solvents even at reflux temperatures. Many impurities were also very insoluble in alcoholic solvents and were thus retained in modafinil. In many cases 1 g of crude modafinil required a minimum of 8 ml of methanol to be completely dissolved at reflux temperature. When filtered at room temperature, many impurities were only moderately reduced.

It also been found that excellent purification of modafinil can be achieved by mixing the crude modafinil product with a halo-organic solvent such as dichloromethane, dichloroethane and preferably chloroform. Chloroform was initially believed to be a better solvent for the clean-up procedure because it was slightly acidic in comparison to alcohols. Surprisingly, modafinil was also extremely insoluble in chloroform, but fortunately, the impurities were very soluble in chloroform. Major impurities in the crude modafinil product include the modafinil acid, modafinil sulfone acid, modafinil sulfone and unreacted starting material, benzhydrylthioacetamide. Crude modafinil was initially mixed with chloroform in 1 g crude to 4 ml chloroform. It has been found that the major impurities are substantially removed by the chloroform washing.

In a preferred embodiment a low boiling aliphatic solvent, preferably heptane, can be added in a ratio of about 2 ml of solvent to about 1 g crude to help reduce the viscosity of the slurry. To address the problem of the viscous slurry, heptane can be charged first to the crude. Chloroform is then added to the stirred mixture slowly. A mild slurry, results. Heating the slurry to reflux further alleviates the viscosity to a simple solid/liquid mixture even when it was cooled to 5° C. allowing easy filtering with high yields. The slurry would become less viscous only upon heating to reflux for about 30 minutes. Even though the modafinil never completely dissolves in the solvent mixture, the cleaning procedure is effective. The solvent mixture is then cooled to about 5° C. allowing the modafinil to precipitate fully after which it can be filtered to obtain 92% to 97% recovery yield with ~99.8% purity by weight (HPLC analysis), respectively. In this preferred embodiment any suitable low boiling aliphatic solvent such as pentane, hexane, heptane, or octane may be employed.

The following examples are intended to illustrate the present invention and are not to limit the claims in any manner. All of the percentages are by weight unless otherwise indicated.

EXAMPLE 1

Preparation of Benzhydrylthiocarboxamidine Salt

To a reaction vessel there was charged 82.63 g of thiourea, 150 ml of HBr (48%) and 200 ml of water. Then, 100 g of benzhydrol were charged to the mixture in the reaction vessel. The reaction mixture was then refluxed at 90° C. for 5 hr. The reaction mixture was then cooled to room temperature and 100 ml of additional water were added to the mixture followed by filtration. The crude solid residue was rinsed with 75 ml and air-dried to provide approximately 90% (molar) yield at greater than 95% purity.

EXAMPLE 2

Preparation of Benzhydrylthioacetamide

To a 1 liter 3-neck round bottom flask there were added 86.5 g of benzhydrylthiocarboxamidine bromide from Example 1, 35.3 g of methyl chloroacetate, 93.5 g of potassium carbonate and 300 ml of methanol. The reaction mixture was maintained at room temperature in a water bath and continued stirring at room temperature for 24 hours. The resulting solution exhibited a slight, pink color. The reaction mixture was then cooled to 15° C. and ammonia gas was bubbled through the reaction for 1 hour at a high rate. The reaction was diluted with 600 ml of water. A precipitate formed and the reaction mixture was filtered to obtain 58 g of product. Analysis by HPLC indicated the presence of benzhydrylthioacetamide in 89% purity.

EXAMPLE 3

Preparation of Benzhydrylsulphinylacetamide

To a 500 ml three-necked round bottom flask was charged 50 grams of benzhydrylthioacetamide and 100 ml of acetic acid. The mixture was stirred until all solids were dissolved and then the reaction mixture was cooled to 15° C. Subsequently, 25 ml of hydrogen peroxide solution (30%) were added to the reaction mixture in step-wise fashion (5-10 ml portions) while maintaining the temperature of the reaction mixture below 20° C. The reaction mixture was then stirred at room temperature (20° C.) or until the amide disappeared. There was then added 500 ml of water to the reaction mixture thereby precipitating the product. The reaction mixture was cooled to 15° C. and filtered. The crude solid product was then rinsed with 50 ml of water. The product was then purified by first combining it with n-heptane (3.5 ml/1 g crude) and then chloroform (7 ml/1 g of crude). The combined slurry was refluxed for 30 min. at a temperature of 70-75° C. The solution was slowly cooled to 10° C. with stirring and the solid precipitate then filtered and oven dried. The yield was 85% (molar) and the purity was 99.8%.

EXAMPLE 4

| Step 1 | | | | | | |
|---|---|---|---|---|---|---|
| Reagents | MW | Density | grams | Ml | mole | Equivalent |
| Benzhydrol 1 | 184.24 | | 2522.00 | | 13.69 | 1.00 |
| Thiourea 2 | 76.12 | | 1562.97 | | 20.53 | 1.50 |
| 36-37% HCl | 36.46 | 1.10 | | 1964.01 | 23.27 | 1.70 |
| Water | | | | 5000.00 | | |

Thiourea 2 was charged to a 12 L, 3-necked round bottom flask (3NRB) containing a 36%-37% solution of HCl in water. Then benzhydrol 1 was charged to the reaction mixture and the contents of the flask raised to a temperature of 70° C. for 2 hours. The benzhydrol melted at 57° C. resulting in a heterogeneous reaction mixture. The temperature rose to a maximum of 84° C. for about 15 minutes. The reaction mixture was then cooled to room temperature and filtered. The solids were collected, rinsed with 3 L of water and air-dried overnight to yield 3,933 g. of benzhydrylthiocarboxaminidine 3 at 97.5% purity.

| Step 2 | | | | | | |
|---|---|---|---|---|---|---|
| Reagents | MW | Density | grams | Ml | Mole | Equivalent |
| 3 | 278.80 | | 1812.00 | | 6.50 | 1.00 |
| Methyl chloroacetate | 108.52 | 1.23 | 775.69 | 630.64 | 7.15 | 1.10 |
| NaHCO$_3$ | 84.01 | | 1201.21 | | 14.30 | 2.20 |
| Ammonia gas | 17.00 | | 553.41 | | 32.50 | 5.00 |
| Methanol | | | | 4000.00 | | |

Benzhydrylthiocarboxamindine 3 was charged to a 12 L 3NRB together with methyl chloroacetate and methanol (3 L). The reaction mixture was stirred for 15 minutes to help dissolve the reactants. Sodium bicarbonate was then charged to the reaction mixture with stirring over 30 seconds. Mild carbon dioxide evolution was observed. The reaction mixture was then heated to 57° C. for 3 hours. The reaction mixture was left standing over night then cooled to 10° C. Ammonia gas was bubbled through the reaction mixture for 2 hours while maintaining the temperature of the reaction mixture below 30° C. After an additional 1.5 hours an additional liter of methanol was added to the reaction mixture to facilitate stirring because solids precipitated. The reaction mixture was then stirred for an additional 5 hours until all of the methyl benzhydrylthioacetate 4 had been consumed. The reaction mixture was then stirred overnight at room temperature to complete the reaction. The contents of the flask was then cooled to 15° C. and 3.5 L of water were slowly added with stirring after which the reaction mixture was heated to 28° C. to facilitate stirring. The reaction product was then filtered and the solids washed with 4 L of water and air-dried to provide 1,470 g of crude product 5 at 94.5% purity.

| Step 3 | | | | | | |
|---|---|---|---|---|---|---|
| Reagents | MW | Density | grams | ml | mole | Equivalent |
| 5 | 257.35 | | 1469.00 | | 5.42 | 1.00 |
| H$_2$O$_2$ 30% | 34.00 | 1.18 | | 547.05 | 5.70 | 1.05 |
| Acetic acid | | | | 2792.00 | | |

Thioacetamide 5 and acetic acid were charged to a 12 L 3NRB reaction flask. The mixture was stirred until all solids were dissolved. The reaction temperature dropped to 11° C.

(endotherm). Hydrogen peroxide solution (30%) was slowly charged to the flask while maintaining the temperature of the mixture less than 20° C. Although the temperature of the mixture dropped immediately after the peroxide was charged it rose several degrees and once at 17° C., exotherms became much more dramatic as reaction temperature rose to 41° C. in the first hour After the reaction mixture was cooled to 20° C., the remaining 40% of the peroxide was charged. The reaction mixture was stirred overnight at room temperature (20° C.). Then, 8 L of water was slowly charged to the flask to precipitate the product benzhydrylsulphinylacetamide 6. The solids were recovered by filtration and then washed with 3 L of water.

Purification of Product

After air drying overnight the solid crude product was charged to a clean 12 L 3NRB flask followed by 4 L of heptane. Thereafter there was charged to the flask 4.2 L of chloroform to the stirred solution, which was then refluxed at 60° C. for 3 hours. The reaction mixture was allowed to cool to room temperature with stirring and then filtered to recover the solids. The solids were then rinsed with a 1:4 chloroform/heptane mixture then air-dried overnight. These solids were then charged to a 12 L 3NRB flask followed by 4.2 L of methanol. The solution was refluxed at 65° C. for 3 hours. The contents of the flask were then cooled to room temperature, filtered and the solids rinsed with 1 L of methanol. After air-drying overnight, there was obtained 1,238 g of 99.93% pure product 6.

Although the invention has been described in terms of specific embodiments which are set forth in considerable detail, it should be understood that this description is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A process for preparing benzhydrylthioacetate comprising reacting benzhydrylthiocarboxamidine salt with haloacetate in a reaction medium comprising an organic solvent and an organic base or inorganic basic salt.

2. The process of claim 1 wherein the base is selected from the group consisting of sodium sulfate, calcium sulfate, magnesium sulfate, sodium sulfide, magnesium sulfide, calcium sulfide, sodium phosphate, magnesium phosphate, calcium phosphate, potassium phosphate, sodium bicarbonate, calcium bicarbonate, magnesium bicarbonate, sodium nitrate, calcium nitrate, magnesium nitrate, sodium phosphonate, potassium phosphonate, magnesium phosphonate, calcium phosphonate, sodium phosphinate, potassium phosphinate, calcium phosphinate, magnesium phosphinate, potassium sulfate, potassium sulfide, potassium bicarbonate, potassium nitrate, potassium tripolyphosphate, sodium tripolyphosphate, sodium thiophosphate, potassium citrate, tetrapotassium pyrophosphate, ammonium phosphate, ammonium chloride, ammonium sulfate, ammonium bicarbonate, ammonium phosphinate, dimethylformamide, ammonium phosphonate triethylamine and Hunig's base.

3. The process of claim 1 wherein the basic salt is selected from the group consisting of alkali metal and alkaline earth metal sulfates, sulfides, phosphates, carbonates, bicarbonates, nitrates, phosphonates and phosphinates.

4. The process of claim 1 wherein the haloacetate is selected from chloro-, bromo-, fluoro- and iodoacetate.

5. The process of claim 1 wherein the haloacetate is selected from alkyl acetates having from 1 to 5 carbon atoms in the ester group.

6. The process of claim 1 wherein the haloacetate is 2-chloroacetate.

7. The process of claim 6 wherein the 2-chloroacetate is methyl 2-chloroacetate.

8. The process of claim 3 wherein the basic salt is a potassium salt.

9. The process of claim 8 wherein the basic salt is a potassium bicarbonate salt.

10. The process of claim 1 wherein the basic salt is present in a molar equivalent ratio to benzhydrylthiocarboxamidine salt of greater than about 0.1 equivalent per equivalent of benzhydrylthiocarboxamidine salt.

11. The process of claim 10 wherein the basic salt is present in a molar equivalent ratio is in the range of about 2 equivalents per equivalent of benzhydrylthiocarboxamidine salt.

12. The process of claim 1 wherein the organic solvent is selected from the group consisting of lower alkanols, acetone, dimethylformamide, diethylformamide and triethylamine.

13. The process of claim 12 wherein the lower alkanol is selected from the group consisting of methanol, propanol, isopropanol, ethanol, butanol, sec-butyl alcohol, tert-butyl alcohol.

14. A process for preparing modafinil comprising the following steps:
a) reacting benzhydrol with thiourea in the presence of hydrogen halide to provide benzhydrylthiocarboxamidinehalide;
b) reacting haloacetate with the product of step a) to provide benzhydrylthioacetate in an organic solvent having dissolved therein an organic base or an inorganic basic salt and, without isolation, amidating the acetate to obtain benzhydrylthiolacetamide; and
c) oxidizing the product of step b) to obtain benzhydrylsulphinylacetamide.

15. The process of claim 14 wherein the base is selected from the group consisting of sodium sulfate, calcium sulfate, magnesium sulfate, sodium sulfide, magnesium sulfide, calcium sulfide, sodium phosphate, magnesium phosphate, calcium phosphate, potassium phosphate, sodium bicarbonate, calcium bicarbonate, magnesium bicarbonate, sodium nitrate, calcium nitrate, magnesium nitrate, sodium phosphonate, potassium phosphonate, magnesium phosphonate, calcium phosphonate, sodium phosphinate, potassium phosphinate, calcium phosphinate, magnesium phosphinate, potassium sulfate, potassium sulfide, potassium bicarbonate, potassium nitrate, potassium tripolyphosphate, sodium tripolyphosphate, sodium thiophosphate, potassium citrate, tetrapotassium pyrophosphate, ammonium phosphate, ammonium chloride, ammonium sulfate, ammonium bicarbonate, ammonium phosphinate, dimethylformamide, ammonium phosphonate triethylamine and Hunig's base.

16. The process of claim 14 wherein the basic salt is selected from the group consisting of alkali metal and alkaline earth metal sulfates, sulfides, phosphates, carbonates, bicarbonates, nitrates, phosphonates and phosphinates.

17. The process of claim 14 wherein the haloacetate is 2-chloroacetate.

18. The process of claim 14 wherein the haloacetate is selected from chloro-, bromo-, fluoro- and iodoacetate.

19. The process of claim 14 wherein the haloacetate is selected from alkyl acetates having from 1 to 5 carbon atoms in the ester group.

20. The process of claim 16 wherein the basic salt is selected from sodium or potassium salt.

21. The process of claim 19 wherein the 2-chloroacetate is methyl 2-chloroacetate.

22. The process of claim 20 wherein the basic salt is a potassium bicarbonate salt.

23. The process of claim 16 wherein the basic salt is present in a molar equivalent ratio to benzhydrylthiocarboxamidine salt of greater than 0.1.

24. The process of claim 23 wherein the basic salt is present in a molar equivalent ratio to benzhydrylthiocarboxamidine of about 2.

25. The process of claim 14 wherein the organic solvent is selected from the group consisting of lower alkanols, acetone and dimethylformamide.

26. The process of claim 14 further including the step of purifying the product of step c) which comprises contacting the crude product with a halo-organic solvent and then separating the modafinil from the solvent.

27. The process of claim 26 wherein the temperature of the mixture of the product and halo-organic solvent is raised to a reflux temperature.

28. The process of claim 27 wherein the reflux temperature is maintained for about 30 minutes.

29. The process of claim 26 wherein the halo-organic solvent is selected from the group consisting of chloroform, dichloromethane, and dichloroethane.

30. The process of claim 26 further including the step of adding an aliphatic solvent to the mixture.

31. The process of claim 30 wherein an aliphatic solvent is added to product prior to contacting the product with the halo-organic solvent and the temperature of the mixture is raised to the reflux temperature.

32. The process of claim 31 wherein the aliphatic solvent is selected from the group consisting of pentane, hexane, heptane and octane.

33. The process of claim 32 wherein the halo-organic solvent is chloroform and the aliphatic solvent is heptane.

\* \* \* \* \*